United States Patent
Batzer et al.

[11] 3,956,317
[45] May 11, 1976

[54] DIEPOXIDES, PROCESSES FOR THEIR MANUFACTURE AND USE

[75] Inventors: Hans Batzer, Arlesheim; Juergen Habermeier, Allschwil; Daniel Porret, Binningen, all of Switzerland

[73] Assignee: Ciba-Geigy AG, Basel, Switzerland

[22] Filed: Feb. 21, 1975

[21] Appl. No.: 551,797

Related U.S. Application Data

[62] Division of Ser. No. 371,009, June 18, 1973, Pat. No. 3,879,422, which is a division of Ser. No. 113,717, Feb. 8, 1971, Pat. No. 3,759,954.

[30] Foreign Application Priority Data

Feb. 13, 1970 Switzerland.......................... 2136/70

[52] U.S. Cl. ............................................ 260/340.7
[51] Int. Cl.$^2$........................................ C07D 319/04
[58] Field of Search................................. 260/340.7

[56] References Cited
UNITED STATES PATENTS

| | | | |
|---|---|---|---|
| 3,072,678 | 1/1963 | Porrett et al...................... | 260/340.7 |
| 3,423,429 | 1/1969 | Metzger........................... | 260/340.7 |
| 3,748,344 | 7/1973 | McCloud.......................... | 260/340.7 |

Primary Examiner—Ethel G. Love
Attorney, Agent, or Firm—Vincent J. Cavalieri

[57] ABSTRACT

Diepoxides manufactured by epoxidation of diacetals or diketals from $\Delta^3$-cyclohexene-1,1-dimethanol or its homologues and dialdehydes or diketones which apart from the two aldehyde groups or keto groups only contain hydrocarbon radicals, for example the diepoxide of the formula

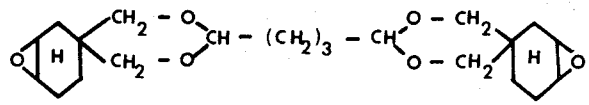

The new diepoxides couple good mechanical properties with a significantly higher heat distortion point according to Martens than the known epoxidised diacetals of similar constitution, in which the acetal groups are interrupted by an alkylene-oxyalkylene chain instead of by an alkylene chain which is free of ether oxygen.

1 Claim, No Drawings

DIEPOXIDES, PROCESSES FOR THEIR MANUFACTURE AND USE

This is a Divisional of application Ser. No. 371,009 filed on June 18, 1973, now U.S. Pat. No. 3,879,422, which in turn is a division of application Ser. No. 113,717, filed Feb. 8, 1971 now U.S. Pat. No. 3,759,954.

The subject of the present invention are new diepoxides of the formula

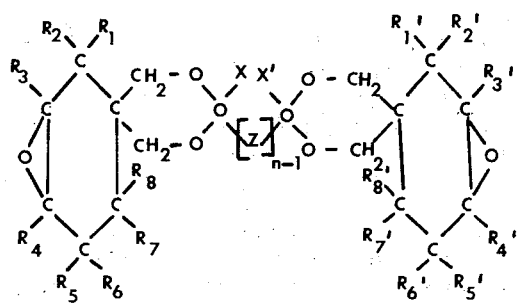
(I)

wherein $R_1$, $R_2$, $R_3$, $R_4$, $R_5$, $R_6$, $R_7$ and $R_8$, $R_1'$, $R_2'$, $R_3'$, $R_4'$, $R_5'$, $R_6'$, $R_7'$ and $R_8'$ denote monovalent substituents, such as halogen atoms, alkoxy groups or aliphatic hydrocarbon radicals, preferably lower alkyl radicals with 1 to 4 carbon atoms or hydrogen atoms, and wherein $R_1$ and $R_5$, or $R_1'$ and $R_5'$ can together also denote an alkylene radical, such as a methylene group, X and X' each denote a hydrogen atom or an aliphatic, cycloaliphatic, araliphatic or aromatic hydrocarbon radical, such as, especially, an alkyl radical with 1 to 4 carbon atoms, or together form an alkylene radical, especially a dimethylene radical or trimethylene radical, and Z denotes a divalent aliphatic, cycloaliphatic, araliphatic or aromatic hydrocarbon radical, preferably an alkylene radical, an n denotes the number 1 or 2.

Particularly easily accessible compounds are the diepoxides of the formula

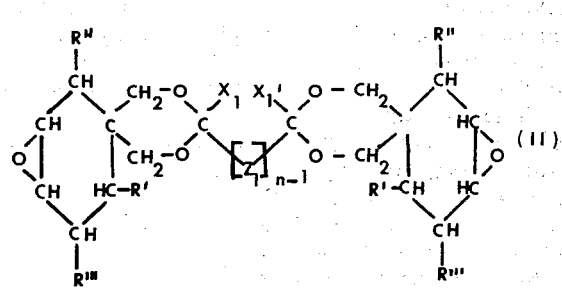
(II)

wherein R' denotes a hydrogen atom or the methyl group, and wherein R" and R''' either each denote a hydrogen atom or together denote the methylene group, $X_1$ and $X_1'$ each denote a hydrogen atom or a lower alkyl group with 1 to 4 carbon atoms, or the radicals $X_1$ and $X_1'$ together denote the dimethylene radical or trimethylene radical, and $Z_1$ represents an alkylene radical with 1 to 10 carbon atoms or a phenylene radical, and n denotes the number 1 or 2.

The new diepoxides of the formula (I) or (II) can be manufactured if, in a compound of the formula

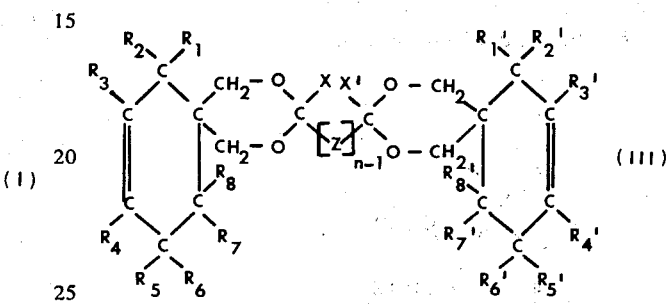
(III)

wherein the radicals $R_1 - R_8$, $R_1'$ to $R_8'$, X, X', Z and n have the same meaning as in formula (I), or in a compound of the formula

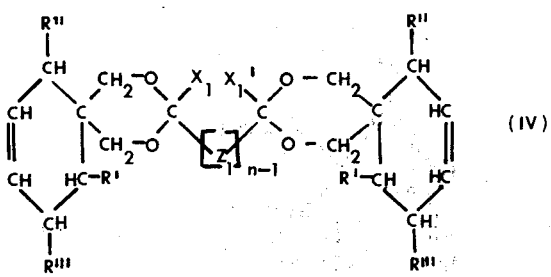
(IV)

wherein the radicals R', R", R''', $X_1$, $X_1'$, $Z_1$ and n have the same meaning as in the formula (II), the C=C double bonds in the cyclohexene rings are epoxidized by treatment with epoxidising agents.

The epoxidation of the C=C double bond in the cyclohexene ring is carried out according to customary methods, preferably with the aid of organic per-acids, such as peracetic acid, perbenzoic acid, peradipic acid, monoperphthalic acid and the like; further, mixtures of $H_2O_2$ and organic acids, such as formic acid, or nitriles, such as benzonitrile, or acid anhydrides, such as acetic anhydride or succinic anhydride, can be used. Hypochlorous acid can also serve as the epoxidising agent, in which case, in a first stage, HOCl is added onto the double bond, and, in a second stage, the epoxide group is produced under the influence of agents which split off HCl, for example strong alkalis.

The acetals or ketals of the formulae (III) or (IV) can, again, be manufactured in a known manner by acetalisation or ketalisation of a dialdehyde of the formulae

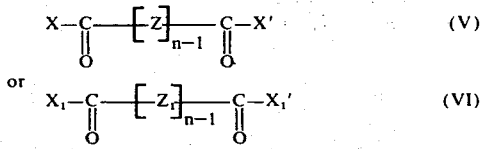

with a dialcohol of the formula

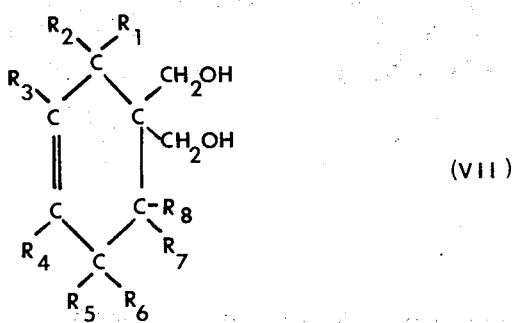

or of the formula

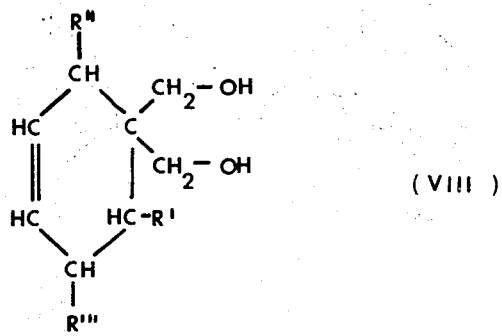

The acetalisation can take place according to methods which are in themselves known, such as, for example, by heating the aldehydes or ketone of the formulae (V) or (VI) together with the dialcohol (VII) or (VIII) in the presence of an acid catalyst, such as, for example, sulphuric acid, phosphoric acid or p-toluenesulphonic acid.

As dialdehydes of the formulae (V) or (VI) there may be mentioned: glyoxal, succinodialdehyde, glutarodialdehyde, adipodialdehyde, pimelodialdehyde, suberodialdehyde, sebacodialdehyde, n-dodecane-1,12-dial, terephthalaldehyde and isophthalaldehyde.

As diketones of the formulae (V) or (VI) there may be mentioned: 1,2-diketones, such as biacetyl, acetylpropionyl, bipropionyl, bibutyryl, biisobutyryl, benzyl, furyl and acetylbenzoyl; 1,3-diketones, such as acetylacetone, propionylacetone, butyrylacetone, valerylacetone, pivaloylacetone, 1-cyclohexyl-1,3-butanedione, 5,5-dimethyl-1,3-cyclohexanedione, 1-phenyl-1,3-butanedione and 1-phenyl-1,3-pentanedione; 1,4-diketones, such as 2,5-hexanedione, 2,5-octanedione, 2,5-decanedione, 2,5-dodecanedione, 3,6-dodecanedione, 2,5-octanedecandione and 1,4-cyclohexanedione.

Further possible starting products of the formulae (V) or (71) are also ketoaldehydes, such as methylglyoxal.

Possible dialcohols of the formulae (VII) or (VIII) are, for example: 1,1-bis-(hydroxymethyl)-cyclohexene-(3), 1,1-bis-(hydroxymethyl)-6-methylcyclohexene-(3), 1,1-bis-(hydroxymethyl)-2,4,6-trimethylcyclohexene-(3), 1,1-bis-(hydroxymethyl)-2,5-endomethylene-cyclohexene-(3) and 1,1-bis-(hydroxymethyl)-4-chloro-cyclohexene-(3).

The new diepoxides according to the invention, of the formulae (I) or (II), react with customary curing agents for polyepoxide compounds and can therefore be crosslinked or cured by adding such curing agents, analogously to other polyfunctional epoxide compounds or epoxide resins. Possible curing agents of this nature are basic compounds or acidic compounds.

As suitable curing agents, there may for example be mentioned: heterocyclic amines, such as 1-methylimidazole or 2-methylimidazole; Lewis acids, such as phosphorus pentafluoride, and boron trifluoride and its complexes with organic compounds, such as $BF_3$-ether complexes and $BF_3$-amine complexes, for example the $BF_3$-monoethylamine complex; acetoacetanilide-$BF_3$-chelate; polybasic carboxylic acids, and in particular, above all, tetracarboxylic acids, such as pyromellitic acid or ester-carboxylic acids containing four carboxyl groups, for example the ester-carboxylic acids obtained from 4 mols of a dicarboxylic acid or dicarboxylic acid anhydride, for example succinic acid or hexahydrophthalic anhydride and 1 mol of a tetrahydric alcohol, such as pentaerythritol, or the ester-carboxylic acids obtained from 2 mols of a tricarboxylic acid anhydride, such as trimellitic anhydride, and 1 mol of a dihydric alcohol, such as triethylene glycol or tetraethylene glycol.

Preferred curing agents are the anhydrides of polybasic carboxylic acids, for example phthalic anhydride, $\Delta^4$-tetrahydrophthalic anhydride, hexahydrophthalic anhydride, 4-methylhexahydrophthalic anhydride, 3,6-endomethylene-$\Delta^4$-tetrahydrophthalic anhydride, methyl-3,6-endomethylene-$\Delta^4$-tetrahydrophthalic anhydride (= methylnadic anhydride), 3,4,5,6,7,7-hexachloro-3,6-endomethylene-$\Delta^4$-tetrahydrophthalic anhydride, succinic anhydride, adipic anhydride, azelaic anhydride, sebacic anhydride, maleic anhydride and dodecenylsuccinic anhydride; pyromellitic anhydride; or mixtures of such anhydrides.

In curing the diepoxides according to the invention with anhydrides, it is appropriate to use 0.5 to 1.1 gram equivalents of anhydride groups per 1 gram equivalent of epoxide groups.

Optimum properties of the cured products are as a rule achieved on using approx. 1 equivalent of anhydride groups per equivalent of epoxide groups.

Curing accelerators can furthermore be employed in the curing reaction; when using polycarboxylic acid anhydrides as curing agents, suitable accelerators are, for example, tertiary amines, their salts or quaternary ammonium compounds, for example 2,4,6-tris-(dimethylaminomethyl)-phenol, benzyldimethylamine, 2-ethyl-4-methyl-imidazole, 4-amino-pyridine or triamylammonium phenolate; and also alkali metal alcoholates, such as, for example, sodium hexanetriolate.

The term "curing", as used here, denotes the conversion of the abovementioned diepoxides into insoluble and infusible, crosslinked products, and in particular, as a rule, with simultaneous shaping to give shaped articles, such as castings, pressings or laminates and the like, or to give "sheet-like structures", such as coatings, coverings, lacquer films or adhesive bonds.

Depending on the choice of the curing agent, the curing can be effected at room temperature (18° to 25°C) or at elevated temperature (for example 50° to 180°C).

The curing can, if desired, also be carried out in 2 stages, by first prematurely stopping the curing reaction, or carrying out the first stage at only moderately elevated temperature, whereby a curable pre-condensate which is still fusible and soluble (a so-called "B-stage") is obtained from the epoxide component and the curing agent component. Such a pre-condensate can for example serve for the manufacture of "pre-pregs", compression moulding compositions or sintering powders.

The diepoxides according to the invention, of the formulae (I) or (II), can also be used in mixtures with other curable diepoxide or polyepoxide compounds. As such, there may for example be mentioned: polyglycidyl ethers or poly-($\beta$-methylglycidyl) ethers of polyhydric alcohols, such as polyethylene glycols, polypropylene glycols, 2,2-bis-(4'-hydroxycyclohexyl)-propane or 1,3-di-(2-hydroxy-n-propyl)-5,5-dimethylhydantoin; polyglycidyl ethers or poly-($\beta$-methylglycidyl) ethers of polyhydric phenols, such as 2,2-bis-(4'-hydroxyphenyl)propane (= diomethane), 2,2-bis-(4'-hydroxy-3',5'-dibromophenyl)-propane, bis-(4-hydroxyphenyl)-sulphone, 1,1,2,2-tetrakis-(4-hydroxyphenyl)-ethane or condensation products, manufactured in an acid medium, of formaldehyde with phenols, such as phenol novolacs or cresol novolacs; polyglycidyl esters or poly-($\beta$-methylglycidyl) esters of polycarboxylic acids, such as for example phthalic acid diglycidyl ester, isophthalic acid diglycidyl ester, tetrahydrophthalic acid diglycidyl ester or hexahydrophthalic acid diglycidyl ester, triglycidyl isocyanurate, N,N'-diglycidyl-5,5-dimethylhydantoin, 1-glycidyl-3-(2-glycidyloxypropyl)-5,5-dimethylhydantoin, and aminopolyepoxides such as are obtained by dehydrohalogenation of the reaction products of epihalogenohydrin and primary or secondary amines, such as aniline or 4,4'-diaminodiphenylmethane; further, alicyclic compounds containing several epoxide groups, such as vinylcyclohexene diepoxide, dicyclopentadiene diepoxide, ethylene glycol-bis-(3,4-epoxytetrahydrodicyclopentadien-8-yl)ether, (3',4'-epoxycyclohexylmethyl)3,4-epoxycyclohexanecarboxylate, (3',4'-epoxy-6'-methylcyclohexylmethyl)-3,4-epoxy-6-methylcyclohexanecarboxylate, bis(2,3-epoxycyclopentyl) ether or 3-(3',4'-epoxycyclohexyl)-2,4-dioxaspiro-(5,5)-9,10-epoxyundecane.

If desired, known reactive diluents, such as, for example, styrene oxide, butyl glycidyl ether, isooctyl glycidyl ether, phenyl glycidyl ether, cresyl glycidyl ether, or glycidyl esters of synthetic, highly branched, mainly tertiary aliphatic monocarboxylic acids (CARDURA E) can be used conjointly.

A further subject of the present invention are therefore curable mixtures which are suitable for the manufacture of shaped articles, including two-dimensional structures, and which contain the diepoxides accrording to the invention, optionally together with other diepoxides or polyepoxides and also curing agents for epoxide resins, such as, especially, polycarboxylic acid anhydrides.

The diepoxides according to the invention, or their mixtures with other polyepoxides and/or curing agents can furthermore be mixed, in any stage before curing, with customary modifiers, such as extenders, fillers and reinforcing agents, pigments, dyestuffs, organic solvents, plasticisers, flow control agents, agents for conferring thixotropy, flameproofing substances or mould release agents.

As extenders, reinforcing agents, fillers and pigments which can be employed in the curable mixtures according to the invention, there may for example be mentioned: coal-tar, bitumen, textile fibres, glass fibres, asbestos fibres, boron fibres, carbon fibres, cellulose, polyethylene powder and polypropylene powder; quartz powder, mineral silicates, such as mica, asbestos powder or slate powder; kaolin, aluminium oxide trihydrate, chalk powder, gypsum, antimony trioxide, bentones, silica aerogel (AEROSIL), lithopones, baryte, titanium dioxide, carbon black, graphite, oxide pigments, such as iron oxide, or metal powders, such as aluminium powder or iron powder.

Suitable organic solvents for modifying the curable mixtures are, for example, toluene, xylene, n-propanol, butyl acetate, acetone, methyl ethyl ketone, diacetone-alcohol, ethylene glycol monomethyl ether, monoethyl ether and monobutyl ether.

As plasticisers for modifying the curable mixtures it is, for example, possible to employ dibutyl, dioctyl and dinonyl phthalate, tricresyl phosphate, trixylenyl phosphate and polyproplyene glycols.

As flow control agents when employing the curable mixtures, especially in surface protection, it is possible to add, for example, silicones, cellulose acetobutyrate, polyvinyl butyral, waxes, stearates and the like (which are in part also used as mould release agents).

Especially for use in the lacquer field, the diepoxides can further be partially esterified in a known manner with carboxylic acids, such as especially higher unsaturated fatty acids. It is furthermore possible to add other curable synthetic resins, for example phenoplasts or aminoplasts, to such lacquer formulations.

The curable mixtures according to the invention can be manufactured in the customary manner, with the aid of known mixing equipment (stirrers, kneaders, rolls and the like).

The curable epoxide resin mixtures according to the invention are above all employed in the fields of surface protection, the electrical industry, laminating processes and the building industry. They can be used in a formulation adapted in each case to the particular end use, in the unfilled or filled state, optionally in the form of solutions or emulsions, as paints, lacquers, compression moulding compositions, sintering powders, dipping resins, casting resins, injection moulding formulations, impregnating resins and binders, adhesives, tool resins, laminating resins, sealing and filling compositions, floor covering compositions and binders for mineral aggregates.

Because of the generally solid state of aggregation of the diepoxides according to the invention, the main use lies in the field of powder resins, such as sintering powders and compression moulding compositions, and in the field of prepregs.

In the examples which follow, parts denote parts by weight and percentages denote percentages by weight, unless otherwise stated. The relationship of parts by volume to parts by weight is as of the milliliter to the gram.

To determine the mechanical and electrical properties of the shaped articles obtainable from the curable mixtures described in the examples which follow, sheets of size 92 × 41 × 12 mm were manufactured for determining the flexural strength, deflection, impact strength and water absorption. The test specimens (60 × 10 × 4 mm) for determining the water absorption and for the flexural test and impact test (VSM 77,103 and 77,105 respectively) were machined from the sheets.

To determine the heat distortion point according to Martens (DIN 53,458), test specimens of sizes 120 ×15 × 10 mm were cast in each case.

Sheets of sizes 120 × 120 × 4 mm were cast for determining the arcing resistance and tracking resistance (VDE 0303). The 1% value of tgδ is the temperature at which the dielectric loss factor tgδ exceeds a value of 1 × 10⁻².

Manufacture of the starting substances.
(Olefinically unsaturated diacetals and diketals).

EXAMPLE A

Manufacture of the diacetal from Δ³-cyclohexene-1,1-dimethanol and glutarodialdehyde.

A mixture of 568 g of Δ³-cyclohexene-1,1-dimethanol (4.0 mols), 400 g of 50% strength aqueous glutarodialdehyde (2.0 mols), 216 ml of benzene and 1.47 g of toluenesulphonic acid is subjected to an azeotropic circulatory distillation at 120°C bath temperature, whilst stirring. The reaction mixture is initially at a temperature of 83°C, and water immediately starts to separate. After one hour's reaction time, 124 ml of water have separated and the temperature of the batch rises to 88°C. After 2½ hours, the bath temperature is raised to about 130°C, and in doing so the temperature of the batch gradually rises to 106° – 107°C. After a total of 4 hours, the separation of water is complete, 263 ml being separated (theory = 272 ml). The reaction product is filtered, and the filtrate is concentrated on a rotary evaporator at 80° – 100°C. A tough, viscous product is obtained in quantitative yield. The diacetal can be purified by fractional distillation in vacuo. The following fractions are obtained from 699.9 g of the crude product:

Fraction 1: boiling point 0.6 – 0.2: 20° – 180°C: first runnings, amount: 28.1 g
Fraction 2: boiling point 0.35 : 183° – 188°C: pure diacetal: 619.8 g
Fraction 3: residue: 43.5 g.

The yield of pure material is thus 619.8 g; this corresponds to 89.0% of theory. The pure diacetal is a colourless, viscous liquid, which crystallises completely. The melting point is 52° – 58°C. Elementary analysis shows 72.1 C (and 9.2% H) (theory: 72.38 C and 9.26% H).

The infrared spectrum shows, through the absence of OH frequencies at 3450 cm⁻¹ and through the absence of the carbonyl vibrations at 1730 cm⁻¹, that the reaction has taken place as desired. Instead, the very intense C-O-C frequencies of the acetal groups can be detected at about 1120 cm⁻¹, and the C=C absorption is found at approx. 1650 cm⁻¹.

The proton-magnetic resonance spectrum (60 Mc HMNR, recorded in CDCl₃ at 35°C, with tetramethylsilane as the internal standard) indicates the presence of 32 protons (theory = 32).

Additionally, the following structural elements are found:

4 protons: δ = 5.6–5.8 (multiplet): 2    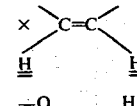

2 protons: δ = 4.4–4.6 (multiplet): 2    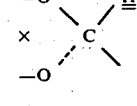

8 protons: δ=3.98 (quartet with fine structure): 2
3.78
3.51
3.30
18 protons: δ = 1.1–2.3 (multiplet):    remaining methylene protons.

Accordingly, the new diacetal has the following structure:

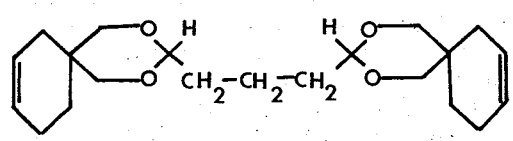

EXAMPLE B

Manufacture of the diketal from Δ³-cyclohexene-1,1-dimethanol and 1,4-cyclohexanedione.

113.6 g of Δ³-cyclohexene-1,1-dimethanol (0.8 mol), 44.7 g of 1,4-cyclohexanedione (0.4 mol), 150 ml of benzene and 0.3 g of p-toluenesulphonic acid are mixed, and this mixture is heated, whilst stirring, until the azeotropic circulatory distillation, as described in Example 1, commences. 13 ml of water have separated after only 30 minutes (90.3% of theory). To complete the reaction, circulatory distillation is allowed to continue for a further 2 hours, whilst stirring. In the course thereof, a crystalline precipitate forms. The batch is cooled to 20°C and the crystals formed are filtered off. After drying at 60°C under 15 mm Hg, 129.5 g of the crude diketal (89.9% of theory) are obtained, melting at 187°–189°C. The product can be purified by recrystallisation from chloroform. Colourless, glossy crystals are obtained, which melt at 187.6°–189°C. Elementary analysis shows 73.5% C and 9.0% H (theory: 73.30% C and 8.95% H).

The proton-magnetic resonance spectrum (60 Mc H—NMR, recorded in CDCl₃ at 35°C with tetramethylsilane as the internal standard) proves the structure given below, through the presence of the following signals:

δ = 5.65 (singlet): 4 protons: 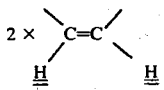

δ = 3.60 (singlet): 8 protons: 4 x —O—C$\underline{H}$₂
δ = 1.35–2.25 (multiplet): 20 methylene protons of the cycloaliphatic rings.

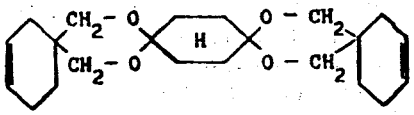

EXAMPLE C

Manufacture of the diacetal from Δ³-cyclohexene-1,1-dimethanol and glyoxal.

A mixture of 213 g of Δ³-cyclohexene-1,1-dimethanol (1.5 mols), 117.5 g of 37% strength aqueous glyoxal solution (0.75 mol), 85 ml of benzene and 5.5 g of p-toluenesulphonic acid is heated to 78°–104°C, whilst stirring. In doing so an azeotropic circulatory distillation commences, as described in Example A. After 75 minutes, 90 ml of water have separated; after a total of 165 minutes, 94 ml of water have separated (92.7% theory), and the reaction is stopped. The hot reaction mixture is filtered, 200 ml of benzene are added and the whole is cooled. 105.8 g of light ochre-coloured crystals are obtained. The mother liquor is concentrated and a further 108.5 g of a light brown crystallising mass are obtained. Total yield: 214.3 g (94% of theory).

The diacetal can be purified by recrystallisation from methanol, ethanol or acetone. From acetone, crystals of melting point 138.4°–140°C are obtained.

IR and NMR spectra show the presence of the following structure:

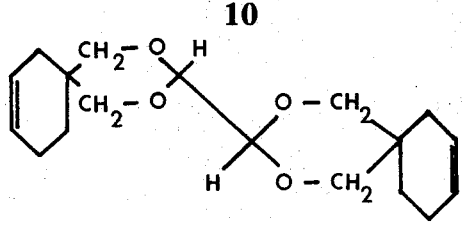

EXAMPLE D

Manufacture of the diacetal from Δ³-cyclohexene-1,1-dimethanol and terephthalaldehyde.

284 g of Δ³-cyclohexene-1,1-dimethanol (2.0 mols), 141.0 g of 95% strength terephthalaldehyde (1.0 mol) and 425 ml of benzene, together with 0.75 g of p-toluenesulphonic acid, are subjected to an azeotropic circulatory distillation at 75°–83°C, whilst stirring. After 60 minutes, 33 ml of water can be separated off, and after 225 minutes 36 ml of water have separated (100% of theory). The reaction mixture is cooled to room temperature, and in doing so the product crystallises out. It is filtered off and dried to constant weight at 50°C under 50 mm Hg. 352.4 g of a pale yellow-coloured crystalline product (92.4% of theory) are obtained, the melting point of this crude product being 189°–193°C. It is purified by recrystallisation from 2 liters of dioxane. 312.3 g of colourless crystals, melting at 197.5°–199°C, are obtained.

The infrared spectrum shows, through the absence of —OH and C=O— frequencies, and through the presence of absorptions for C—O—C, that the desired substance has been produced.

Elementary analysis shows the following:

| Found: | Calculated: |
|---|---|
| 75.5% C | 75.4% C |
| 7.9% H | 7.9% H |

Furthermore, the proton-magnetic resonance spectrum (60 Mc H-NMR, recorded in CDCl₃ at 35°C, with tetramethylsilane as the internal standard) shows, through the presence of the following signals, that the diacetal has the structure given below:

| 12 protons: δ = 1.3–2.4 | (multiplet): | methylene protons of the cyclohexene rings |
| 8 protons: δ = 3.50<br>3.65<br>3.88<br>4.08 | (quartet): | 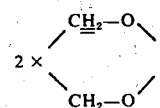 |
| 2 protons: δ = 5.42 | (singlet): | 2 × { Aromatic radical |
| 4 protons: δ = 5.6–5.7 | (multiplet): | 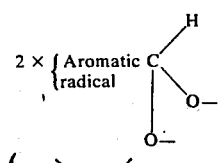 |

4 protons: δ = 7.50 (singlet): 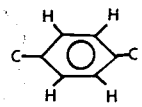

30 protons (theory 30 protons)

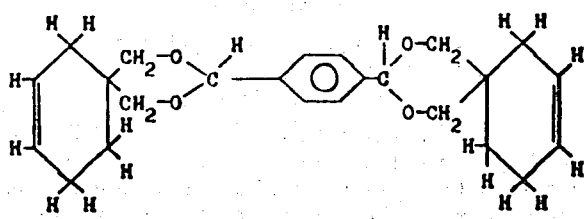

EXAMPLE E

Manufacture of the diacetal from cyclohexene-1,1-dimethanol and pentane-2,4-dione.

A mixture of 284 g of Δ$^3$-cyclohexene-1,1-dimethanol (2 mols), 100 g of pentane-2,4-dione (= acetylacetone), 108 ml of benzene and 4.5 g of p-toluenesulphonic acid is subjected to an azeotropic circulatory distillation at 106°–114°C, as described in Example A. After 4 hours 16 ml of water are separated off, and the separation of water then becomes very slight. After about 20 hours, 18 ml of water are separated off (50% of theory). The reaction mixture is filtered and concentrated completely, whereby a brown liquid is obtained. The desired product is separated off by distillation.

The following fractions are obtained:
  boiling point 0.1 = 17° – 53°C, first runnings, 20 g
  boiling point 0.05 = 58° – 60°C, fraction 1: 109 g (colourless liquid)
  boiling point 0.1 = 87° – 90°C, fraction 2: 154 g (liquid with crystalline portion)
  residue: 61.2 g dark brown resin.

Fraction 2 proves to be a mixture of unreacted Δ$^3$-cyclohexenedimethanol (melting point 88°–91°C) and monoacetal.

Fraction 1 is the desired product. The infrared spectrum shows neither OH frequencies nor carbonyl frequencies, but shows the absorptions characteristic for C—O—C. The product thus produced accordingly corresponds to the following structure:

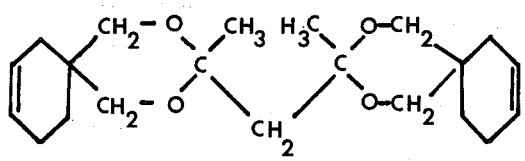

EXAMPLE F

A mixture of 6-methyl-Δ$^3$-cyclohexene-1,1-dimethanol (2.0 mols), 200 g of 50% strength aqueous glutaraldehyde and 112 ml of benzene is subjected to an azeotropic circulatory distillation, whilst stirring, in accordance with Example A); in doing so, the temperature of the heating bath is 134°C, and the temperature of the reaction mixture rises from 76° to 86°C. 80 ml of water are removed from this circuit over the course of 120 minutes, and separated off. The residue is then cooled to 75°C, 1.4 ml of 4 N sulphuric acid are added and distillation is carried out over the course of a further 300 minutes at 134°–144°C bath temperature, with the reaction temperature rising from 86° to 105°C; during this time, a further 54 ml of water are separated off under the conditions indicated. In total, 134 ml of water are thus separated (98.5% of theory). The batch is cooled to 30°C, diluted with 150 ml of benzene, and filtered. The filtrate is extracted four times by shaking with 100 ml portions of water, and is concentrated to dryness on a rotary evaporator. 422 g of a dark-coloured crude product are obtained. This is purified by distillation. 422 g of crude material yields the following fractions:

Fraction I: boiling point 0.08 = 90°–140°C: 10.2 g (2.4% of the amount taken)
  Fraction II: boiling point 0.08 = 180°–182°C: 354.5 g (84.2% of the amount taken)
  Residue: 47.3 g (11.2% of the amount taken).

Thus, 354.5 g of the desired product are obtained (corresponding to 94.5% of theory, relative to dialdehyde employed).

Elementary analysis shows:

| Found | Calculated: |
|---|---|
| 73.4% C | 73.4% C |
| 9.4% H | 9.6% H |

The infrared spectrum (capillary recording) shows, through the absence of C—OH and C=O absorptions and through the presence of the C—O—C— frequencies at approx. 1100 cm$^{-1}$, that the desired product has been produced. Equally, the proton-magnetic resonance spectrum (60 Mc H—NMR, in CDCl$_3$) is in agreement with the structure given below:

4 protons: = δ 5.50–5.65: multiplet: 2 × >C=C<  
   $\quad$ O—

2 protons: = δ 4.30–4.45: multiplet: 2 × H—C<  
   $\quad$ O—

8 protons: = δ 3.3–4.1 : multiplet: 2 × >C—CH$_2$—O  
   $\quad$ CH$_2$—O 6 protons: = δ 0.76
   δ 0.87
   δ 0.92       quartet: 2 × H$_3$C—C—
   δ 1.03                     $\quad$ H 16 protons in multiplets between δ 1.45 and 3.15: remaining protons Accordingly, the new substance has the following structure:

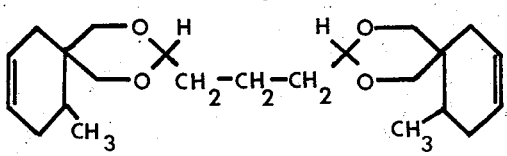

EXAMPLE G

A mixture of 308 g of 2,5-endomethylene-Δ³-cyclohexene-1,1-dimethanol (2.0 mols) and 200 g of 50% strength aqueous glutaraldehyde (1.0 mol) is acetalised analogously to Example F), with the aid of 112 ml of benzene for forming an azeotrope. The procedure followed as is described under F); after separating off 80 ml of water, 1.4 ml of 4 N aqueous sulphuric acid are again added as the catalyst. The further reaction is carried out analogously to Example F). On cooling, the desired substance crystallises out. 800 ml of benzene are added, the crystals are dissolved, and the benzene solution is eluted as described in Example F). Working up also takes place in accordance with Example F). A pale yellow crystal powder is obtained in theoretical yield. It can be purified by crystallisation from ethanol. The reaction product melts at 115°–117°C. Elementary analysis shows: 74.4% C and 8.6% H (calculated, 74.2% C and 8.6% H).

The proton-magnetic resonance spectrum (60 Mc H-NMR, in $CDCl_3$, against TMS) shows, through the presence of the following signals and their integrations (allocation by trial), that the structure given below is correct:

4 protons: = 6.05–6.20:  multiplet:  2 × H—C=C—H 2 protons: = 4.30–4.40:  multiplet:  2 × H—C(O—)(O—)

3 protons: = 3.40–4.10:  multiplet:  2 × C(CH₂—O—)(CH₂—O)

4 protons: = 2.75–3.21 doublet with fine structure

2× (cyclohexene with H, H)

16 protons: = 0.5–2.3 in multiplets: remaining protons

Manufacture of the diepoxides.

EXAMPLE 1

A mixture of 104.4 g of the crude diacetal manufactured according to Example A (0.3 mol), 62 g of benzonitrile (0.606 mol), 420 ml of methanol and 12 ml of 0.1 M $Na_2HPO_4$ solution is stirred at 50°C. 30 g of 35% strength aqueous hydrogen peroxide are then added and a pH of 9.5, determined by means of a glass electrode, is set up with 0.5 N aqueous sodium hydroxide solution. After 1 hour, a further 24 g of 35% strength hydrogen peroxide are added and the pH is continuously kept at 9.5. One hour later, the remaining 16 g of 35% strength $H_2O_2$ are added (total thus 0.72 mol). The mixture is stirred for a further 3 hours at 50°C whilst continuously checking the pH. In total, 37.3 ml of the 0.5 N aqueous sodium hydroxide solution are consumed. After the indicated time, the content of hydrogen peroxide in the batch has fallen to 0.75 per cent by weight (iodometric titration). The batch is cooled to room temperature, and 400 ml of water are stirred in. This solution is twice extracted with 350 ml portions of chloroform; the chloroform phase is twice extracted by shaking with 300 ml portions of water. Thereafter, the organic phase is concentrated to ¼ of its volume on a rotary evaporator, at 60°C, under a slight vacuum. 200 ml of low-boiling petroleum ether are added and the whole is cooled to 5°C. The residual benzamide which precipitates is filtered off and the solution is completely concentrated on a rotary evaporator at 60°–70°C. The resin is then dried to constant weight at 60°C under 0.1 mm Hg. 98.7 g (86.6% of theory) of a clear, pale yellow viscous resin, which gradually crystallises, are obtained. The epoxide content is 4.02 equivalents per kg (76.5% of theory). The infrared spectrum shows, through the absence of the C=C frequency at 1650 cm⁻¹ and through the presence of the absorptions of the oxirane ring, that the product mainly consists of the desired diepoxide of the formula

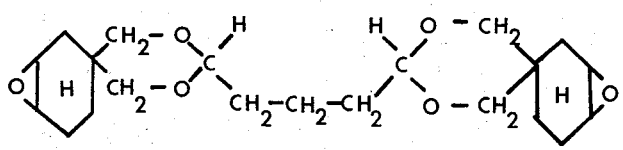

EXAMPLE 2

A mixture of 313 g of the distilled diacetal manufactured according to Example A, 90 g of sodium acetate and 1200 ml of methylene chloride is stirred at 20°C. 317 g of 60.4% strength peracetic acid solution in glacial acetic acid are then added dropwise over the course of 3½ hours, whilst stirring. The reaction is slightly exothermic, and the temperature of the reaction mixture rises to 28°C. After the dropwise addition, the mixture is stirred at 20°–25°C for a further 3½ hours. The iodometrically determined per-acid content of the solution is then less than 1.7 per cent by weight. The reaction mixture is subsequently washed with 12 ml of 10% strength aqueous sodium bicarbonate solution and thereafter with 800 ml of water. The organic layer is concentrated on a rotary evaporator and then dried at 70°C/15mm Hg. Drying to constant weight is then carried out at 70°C/0.1 mm Hg. 335.5 g (98.1% of theory) of a colourless, clear and viscous resin are obtained. The epoxide content is 5.06 equivalents per kg (96.2% of theory). The resin crystallises completely within a short time.

The new diepoxide can be purified by recrystallisation from ether-acetone. 10 g of the crude product yield 9.7 g of pure, white crystalline product with 5.23 epoxide equivalents per kg (corresponding to 99.5% of theory). The diepoxide melts at 77°–86°C.

The proton-magnetic resonance spectrum (60 Mc H-NMR, recorded in CDCl₃ at 35°C, with tetramethylsilane as the internal standard), proves, through the presence of the following signals, that the new diepoxide corresponds to the structural formula given below.

1. no signals in the range = 5.4–5.8; thus, no traces of HC=CH remain.

2. intense signal at = 3.17 (singlet): 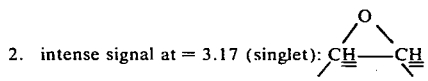

3. further signals:

at δ = 4.4    2 × 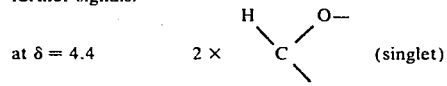 (singlet)

at δ = 3.3–4.0    2 × 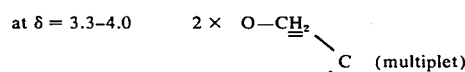 (multiplet)

at δ = 1.0–2.2 remaining 18 methylene protons 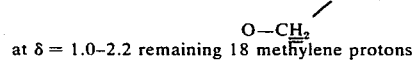

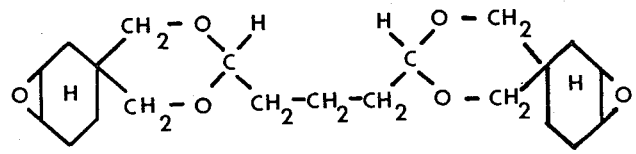

EXAMPLE 3

A mixture of 90 g (0.25 mol) of the diketal manufactured according to Example B, 25 g of sodium acetate and 375 ml of chloroform is stirred at 20°–23°C. 88.1 g of 60.4% strength peracetic acid in glacial acetic acid (0.7 mol) are added dropwise over the course of 1½ hours. 30 minutes thereafter, the reaction mixture still contains 2.45 per cent by weight of per-acid. After a total of 5 hours, the per-acid content declines to below 1.1 per cent by weight; the mixture is then washed 350 ml of sodium bicarbonate solution and subsequently with 200 ml of water. The organic layer is concentrated on a rotary evaporator at 60°C bath temperature, and is subsequently dried to constant weight at 60°C/0.1 mm Hg. 94.7 g of a colourless crystal mass (96.8% of theory) are obtained. The epoxide content is 4.92 equivalents/kg (corresponding to 96.6% of theory). The substance melts at between 223° and 235° C.

The proton-magnetic resonance spectrum proves, through the signals given below, that the structure given below applies (60 Mc H—NMR, recorded in CDCl₃ at 35°C with tetramethylsilane as the internal standard). The singlet at δ = 5.6 is no longer visible. Accordingly, practically all

groups have reacted:

8 protons: δ = 3.46 and 3.55 (doublet) 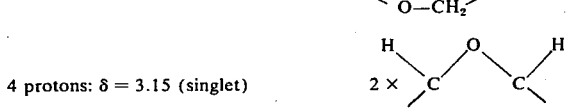

4 protons: δ = 3.15 (singlet)

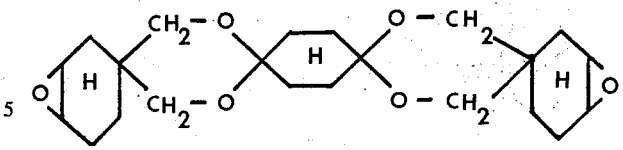

EXAMPLE 4

A mixture of 152 g (0.5 mol) of the diacetal manufactured according to Example C, 50 g of anhydrous sodium acetate and 750 ml of methylene chloride is stirred at 17°–24°C. 172.3 g of 61.4% strength peracetic acid (1.4 mol) are added dropwise over the course of 120 minutes, with slight cooling. 60 minutes thereafter, 2.5% of peracetic acid can still be detected in the mixture. After a total of 6 hours, the peracetic acid content has fallen to below 1.8%, and the mixture is worked up. It is extracted by shaking with 680 ml of 10% strength sodium bicarbonate solution and subsequently with 500 ml of water, in accordance with Example 3. The organic phase is worked up as described in Example 3. 163.7 g of a colourless crystal mass (97.2% of theory), melting at between 158° and 177°C, are obtained. The epoxide content is 5.34 equivalents/kg (90.3% of theory).

The product mainly consists of the diepoxide of the formula

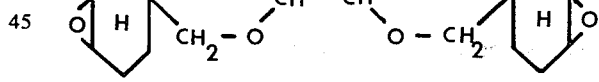

EXAMPLE 5

191 g of the diacetal manufactured according to Example D (0.5 mol), together with 50 g of anhydrous sodium acetate powder, in 796 ml of chloroform, are stirred at 20°C. 173 g of 61.6% strength peracetic acid solution in glacial acetic acid are added dropwise over the course of 120 minutes, whilst stirring. The temperature is kept at 20°–22°C by slight cooling. After a total of 240 minutes, the peracetic acid content of the reaction mixture is 1.78%. After a further hour, it has declined to below 1.4%. The mixture is worked up as described in Example 4. 203.1 g of a colourless crystalline substance (98.2% of theory) are obtained. The epoxide content of the product is 4.20 equivalents/kg (87.4% of theory). The melting point is above 220°C. The IR spectrum shows, through the absence of the C=C absorptions and through the presence of

frequencies, that the product substantially has the following structure:

ory) of a clear, pale yellowish, viscous resin are obtained, having an epoxide content of 4.55 equivalents/kg (corresponding to 92.7% of theory).

The 60 Mc-HNMR spectrum (in CDCl$_3$ at 35°C, against TMS) shows, through the following signals (allocation by trial), that the new diepoxide has the structure given below:

1. the $\underline{H}$ $\underline{H}$ / C=C protons of product F) are absent 2. 2 protons: δ = 4.3–4.5, multiplet: 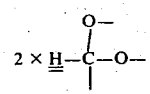

3. 12 protons: δ = 3.0–4.1, multiplet: 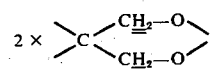

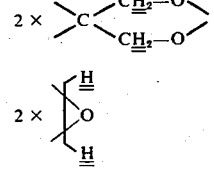

4. 6 protons: δ = 0.80–1.10: multiplet: 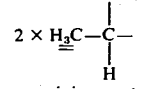

5. 16 protons: δ = 1.3–2.9: multiplet:   remaining protons

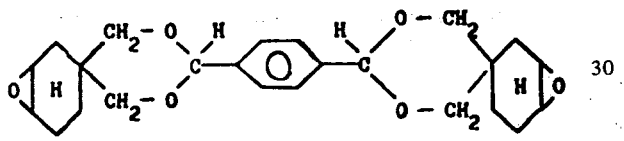

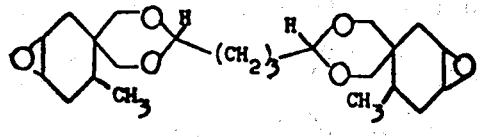

EXAMPLE 6

87 g of the diacetel manufactured according to Example E (0.25 mol) are epoxidised at 20°–23°C with 86.4 g of 61.5% strength peracetic acid (0.7 mol) in 375 ml of methylene chloride in the presence of 25 g of anhydrous sodium acetate, as described in Example 5. Working up takes place in accordance with Example 4.

86.4 g of a colourless liquid of low viscosity, which solidifies after some time to give a colourless crystal mass, are obtained. The epoxide content of the substance is 4.61 equivalents/kg (87.7% of theory).

The product mainly consists of the diepoxide of the formula

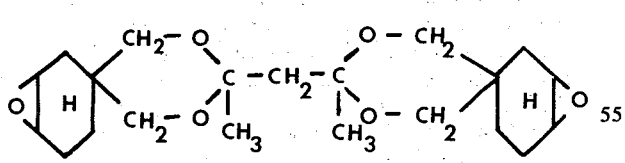

EXAMPLE 7

75.2 g of the diacetal manufactured according to Example F (0.2 mol) in 150 ml of methylene chloride are epoxidised, at 20°–24°C, with 70.4 g of 54.0% strength peracetic acid (0.5 mol), in the presence of 20 g of anhydrous sodium acetate, as described in Example 5. The working up takes place in accordance with Example 4 and 81.6 g (corresponding to 100% of the-

EXAMPLE 8

149 g of the diacetal manufactured according to Example G) (0.4 mol) in 300 ml of methylene chloride, are epoxidised with 57% strength peracetic acid, in the presence of 40 g of anhydrous sodium acetate, as described in Example 5.

The process is carried out at 27°–30°C and the reaction time is 20 hours.

Working up takes place in accordance with Example 4, and 158.6 g (98.1% of theory) of a colourless crystal powder of epoxide content 3.35 equivalents/kg (68% of theory) are obtained. The product substantially consists of the diepoxide of the following formula

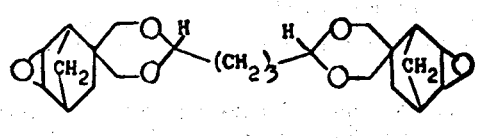

Examples of uses.

EXAMPLE I 61.8 parts of the cycloaliphatic epoxide resin manufactured according to Example 2, having an epoxide content of 5.06 equivalents per kg, are mixed at room temperature with 38.2 parts of hexahydrophthalic anhydride and 3 parts of a solution of 0.82 part of sodium metal in 100 parts of 2,4-dihydroxy-3-hydroxymethylpentane. This mixture is stirred at 120°C to give a clear, transparent, colourless and homogeneous liquid. The mixture is stirred for a further 10 minutes at 120°C and is then poured into thin-walled aluminium moulds (wall thickness approx. 0.15 mm). It is cured in accordance with the following cycle: 5 hours at 120°C and 15 hours at 150°C. The gelling time of 100 g of this mixture is about 40 minutes at 120°C.

Pale yellow, clear, transparent shaped articles are thus obtained, which have the following properties:

| | | |
|---|---|---|
| flexural strength (VSM 77,103) | = 10.22 – 10.51 | kp/mm² |
| deflection (VSM 77,103) | = 4.3 – 5.0 | mm |
| impact strength (VSM 77,105) | = 12.50 – 16.10 | cmkp/cm² |
| heat distortion point according to Martens (DIN 53,458) | = 170 | °C |
| water absorption (4 days/20°C) | = 0.41 | % |
| breakdown voltage (instantaneous) [VDE 0303] | = 209 | kV/cm |
| specific resistance | | |
| at 50°C | = 7.5 × 10¹⁶ | Ω. cm |
| at 110°C | = 2.0 × 10¹⁶ | Ω. cm |
| dielectric loss factor tgδ (50 c/s) | | |
| at 30°C | = 0.005 | |
| at 160°C | = 0.003 | |
| at 140°C | = 0.004 | |
| 1% value of tgδ | = 203°C | |
| dielectric constant $\epsilon_r$ | | |
| at 30°C | = 3.4 | |
| at 200°C | = 3.4 | |

Comparison experiment.

For comparison with the diepoxides according to the invention, according to Example 2, a known cycloaliphatic epoxide resin of the formula

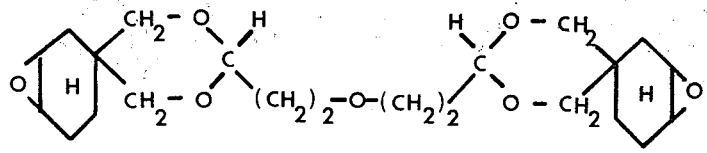

according to French Pat. Specification No. 1,268,722, Example 26, having 4.41 epoxide equivalents/kg, is cured analogously to Example I.

To do so, a mixture of 60 parts of the abovementioned, known diepoxide, 34.5 parts of hexahydrophthalic anhydride and 2.85 parts of a solution of 0.82 part of sodium metal in 100 parts of 2,4-dihydroxy-3-hydroxymethylpentane(accelerator) is prepared and is coverted into castings as in Example I. Brown-yellow castings having the following mechanical properties are obtained:

| | |
|---|---|
| flexural strength (VSM) | 9.02 kp/mm² |
| deflection (VSM) | 3.8 mm |
| impact strength (VSM) | 12.67 cmkp/cm² |
| heat distortion point according to Martens (DIN) | 153 °C |
| water absorption (4 days/20°C) | 0.40 % |

In comparison to the castings from the known diepoxide according to French Patent Specification 1,268,722, those from the diepoxide according to the invention, according to Example 2, show somewhat better flexural and impact properties, and a considerably higher heat distortion point according to Martens.

EXAMPLE II

Manufacture of sintering powders.

The following adducts are manufactured:

a. 410 g of a diepoxide manufactured according to Example 2, having 4.70 epoxide equivalents/kg (corresponding to 0.96 mol) are fused and stirred at 120°C. 97.0 g of sebacic acid (0.48 mol) are added in portions over the course of 30 minutes.

The epoxide content of a sample is then 3.21 equivalents/kg. The reaction mixture is stirred for a further hour at 133°–138°C, in the course of which the epoxide content declines to 1.94 equivalents/kg. The clear, pale yellowish melt is then poured out onto metal sheets in order to cool. After cooling, a glassy-brittle, easily grindable, clear, solid resin, having an epoxide content of 1.72 epoxide equivalents/kg (corresponding to 90.5% of theory) is obtained in quantitative yield. The new, solid epoxide resin has a Kofler softening point of 70°C.

b. Analogously to Example IIa), 300.8 g of adipic acid (2.06 mols) are added in portions over the course of 25 minutes to a melt of 1712 g of the diepoxide manufactured according to Example 2, having 4.83 epoxide equivalents/kg (corresponding to 4.12 mols), at 120°C. Thereafter the mixture is stirred for a further 20 minutes at 140°C. A sample taken from the batch then shows an epoxide content of 2.1 equivalents/kg. The melt is worked up as described in Example a). The hard, brittle, clear adduct obtained in quantitative yield then contains 1.93 equivalents/kg (corresponding to 94.6% of theory). The new epoxide resin has a Kofler softening point of 75°C.

The following powder mixtures are manufactured from the two adducts a) and b):

| | Powder mixture 1 | | Powder mixture 2 | |
|---|---|---|---|---|
| Adduct a) | 300.0 | parts by weight | — | parts by weight |
| Adduct b) | — | | 300.0 | " |
| tertiary amine as an accelerator | 3.0 | " | 3.0 | " |
| titanium dioxide | 75.0 | " | 75.0 | " |
| polyvinyl acetal as a film-forming agent "Mowital B 30 H" | 3.0 | " | 3.0 | " |

|  | Powder mixture 1 | | Powder mixture 2 | |
|---|---|---|---|---|
| sebacic acid | 52.1 | " | 60.6 | " |

These mixtures are homogenised in a laboratory co-kneader (Messrs. BUSS, Pratteln, Switzerland; Type PR 46) at approx. 80°C. The homogenised mixtures are cooled to room temperature, then coarsely ground in a beater mill and subsequently finely ground in a pinned disc mill at high speed (approx. 10,000 r.p.m.).

A short examination of the epoxide resin powders 1 and 2 which have been obtained from the powder mixture 1 and 2 shows the following property data:

|  | Epoxide resin powder 1 | Epoxide resin powder 2 |
|---|---|---|
| Kofler softening range and melting range (°C) | 50–78 | 67–82 |
| gelling time at 200°C (seconds) | 106 | 57 |
| Erichsen extensibility (mm) after curing a film of 70–75 μ at 200°C (1 hour) | 7.0 | 7.2 |
| tracking resistance (level) (on a sintered sheet after curing for 1 hour at 200°C) | KA 3b | KA 3b–3c |

The properties mentioned in this example were determined as follows:

Softening range and melting range.

A Kofler heating bench (manufactured by Reichert, Austria, Type 7871), having a surface temperature rising continuously from approx. 50°C to approx. 250°C, was uniformly sprinkled, by means of a small sieve, with the powder to be tested. After 1 minute, the powder which had not stuck by sintering was wiped off with a brush. The lowest temperature point at which the first powder particles adhered was determined as the softening point (or softening range). The transition point from the matt-looking powder which had stuck by sintering to the fused, glossy, droplike material was determined as the melting point (or melting range).

Gelling time.

An electrical heating plate (manufactured by ElecroPhysik, Cologne) was thermostatically controlled to ± 1.5°C. About 0.3 g of the powder to be tested was placed on the heating plate, and a stopwatch was started simultaneously. The fused material was uniformly agitated by means of a spatula. The viscosity increased detectably as curing progressed. The spatula was periodically lifted and thread-pulling was observed. The point in time at which thread-pulling suddenly stops — because of crosslinking — and the material becomes a coherent layer, was determined as the gelling time.

Erichsen extensibility (DIN 53,156).

The known lacquer test for the extensibility of a film, according to Erichsen, was also employed for the powder coatings. Iron sheets (70 × 150 × 0.8 mm) which had been thoroughly degreased with trichloroethylene were uniformly coated at room temperature, by means of an electrostatic powder spraying instrument, with the powder to be tested (particle size less than 100 μ): The electrostatic adhering powder was hereafter stoved in a circulating air oven to give a thin film. After conditioning the coatings at 20°C and 65% relative humidity, the Erichsen values were determined as the maximum depth of indentation (up to tear formation) in millimeters.

We claim:

1. A diepoxide of the formula:

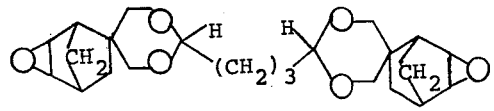

* * * * *